(12) United States Patent
Boyd et al.

(10) Patent No.: US 8,167,941 B2
(45) Date of Patent: May 1, 2012

(54) INTRAOCULAR, ACCOMMODATING LENS AND METHODS OF USE

(75) Inventors: Stephen Boyd, Murrieta, CA (US); Cary Reich, Los Gatos, CA (US)

(73) Assignee: Forsight Labs, LLC, Menlo Park, CA (US)

( * ) Notice: Subject to any disclaimer, the term of this patent is extended or adjusted under 35 U.S.C. 154(b) by 0 days.

(21) Appl. No.: 12/343,406

(22) Filed: Dec. 23, 2008

(65) Prior Publication Data

US 2009/0292355 A1    Nov. 26, 2009

Related U.S. Application Data

(60) Provisional application No. 61/018,837, filed on Jan. 3, 2008.

(51) Int. Cl.
*A61F 2/16* (2006.01)
(52) U.S. Cl. .............. 623/6.28; 623/6.34; 623/6.13
(58) Field of Classification Search ............ 623/6.34, 623/6.13, 6.2
See application file for complete search history.

(56) References Cited

U.S. PATENT DOCUMENTS

| | | | |
|---|---|---|---|
| 4,409,691 A | 10/1983 | Levy | |
| 4,731,078 A * | 3/1988 | Stoy et al. | 623/6.13 |
| 4,782,820 A | 11/1988 | Woods | |
| 4,806,287 A | 2/1989 | Sulc | |
| 4,842,601 A | 6/1989 | Smith | |
| 4,888,012 A | 12/1989 | Horn | |
| 4,893,918 A | 1/1990 | Sulc | |
| 4,932,966 A | 6/1990 | Christie | |
| 4,957,505 A | 9/1990 | McDonald | |
| 4,971,732 A | 11/1990 | Wichterle | |
| 4,994,082 A | 2/1991 | Richards | |
| 5,236,970 A | 8/1993 | Christ et al. | |
| 5,275,623 A | 1/1994 | Sarfarazi | |
| 5,316,704 A | 5/1994 | Wang | |
| 5,444,106 A | 8/1995 | Zhou et al. | |
| 5,480,950 A | 1/1996 | Wang | |
| 5,489,302 A | 2/1996 | Skottum | |
| 5,496,366 A | 3/1996 | Cumming | |
| 5,674,282 A | 10/1997 | Cumming | |
| 5,674,283 A | 10/1997 | Stoy | |
| 5,932,205 A | 8/1999 | Wang et al. | |
| 6,013,101 A | 1/2000 | Israel | |
| 6,143,315 A | 11/2000 | Wang et al. | |
| 6,176,878 B1 | 1/2001 | Gwon | |

(Continued)

FOREIGN PATENT DOCUMENTS

EP    1932492    6/2008

(Continued)

OTHER PUBLICATIONS

Angew Chem Int. Ed. 41(12):1973-2208 (2002).

(Continued)

*Primary Examiner* — David H Willse
*Assistant Examiner* — Tiffany Shipmon
(74) *Attorney, Agent, or Firm* — Fred C. Hernandez; Mintz, Levin, Cohn, Ferris, Glovsky and Popeo, P.C.

(57) ABSTRACT

An intraocular lens comprises an optical element adapted to be implanted within the capsular bag of a human eye. The optical element includes one or more internal layers formed by one or more planes that are moveable relative to one another in order to effect the power of the optical element.

14 Claims, 22 Drawing Sheets

U.S. PATENT DOCUMENTS

| | | |
|---|---|---|
| 6,197,059 B1 | 3/2001 | Cumming |
| 6,231,603 B1 | 5/2001 | Lang |
| 6,232,406 B1 | 5/2001 | Stoy |
| 6,322,589 B1 | 11/2001 | Cumming |
| 6,342,073 B1 | 1/2002 | Cumming |
| 6,387,126 B1 | 5/2002 | Cumming |
| 6,406,494 B1 | 6/2002 | Laguette |
| 6,423,094 B1 | 7/2002 | Sarfarazi |
| 6,443,985 B1 | 9/2002 | Woods |
| 6,451,922 B2 | 9/2002 | Stoy |
| 6,524,340 B2 | 2/2003 | Israel |
| 6,551,354 B1 | 4/2003 | Ghazizadeh |
| 6,592,621 B1 | 7/2003 | Domino |
| 6,617,390 B2 | 9/2003 | Stoy |
| 6,638,305 B2 | 10/2003 | Laguette |
| 6,747,090 B2 | 6/2004 | De Groot |
| 6,790,232 B1 | 9/2004 | Lang |
| 6,797,004 B1 | 9/2004 | Brady |
| 6,818,017 B1 | 11/2004 | Shu |
| 6,884,263 B2 | 4/2005 | Valyunin |
| 6,966,049 B2 | 11/2005 | Lepejian |
| 6,969,403 B2 | 11/2005 | Peng |
| 6,972,033 B2 | 12/2005 | McNicholas |
| 6,986,763 B2 | 1/2006 | Holmen |
| 7,018,409 B2 | 3/2006 | Glick |
| 7,025,783 B2 | 4/2006 | Brady |
| 7,097,660 B2 | 8/2006 | Portney |
| 7,160,324 B2 | 1/2007 | Terwee |
| 7,293,873 B2 | 11/2007 | Dai et al. |
| 7,341,599 B1 | 3/2008 | Peyman |
| 7,381,221 B2 | 6/2008 | Lang et al. |
| 2002/0138140 A1 | 9/2002 | Hanna |
| 2003/0109926 A1 | 6/2003 | Portney |
| 2003/0130732 A1 | 7/2003 | Sarfarazi |
| 2004/0034417 A1 | 2/2004 | Heyman |
| 2004/0082993 A1 | 4/2004 | Woods |
| 2004/0082995 A1 | 4/2004 | Woods |
| 2004/0111153 A1 | 6/2004 | Woods et al. |
| 2004/0127984 A1 | 7/2004 | Paul |
| 2004/0132131 A1 | 7/2004 | Markman |
| 2004/0169820 A1 | 9/2004 | Dai et al. |
| 2004/0237971 A1 | 12/2004 | Radhakrishnan et al. |
| 2005/0021138 A1 | 1/2005 | Woods |
| 2005/0021139 A1 | 1/2005 | Shadduck |
| 2005/0060032 A1 | 3/2005 | Magnante et al. |
| 2005/0065534 A1 | 3/2005 | Hohl |
| 2005/0085906 A1 | 4/2005 | Hanna |
| 2005/0107873 A1* | 5/2005 | Zhou .............................. 623/6.13 |
| 2005/0113914 A1 | 5/2005 | Miller et al. |
| 2006/0100701 A1* | 5/2006 | Esch et al. ................... 623/6.13 |
| 2006/0259138 A1 | 11/2006 | Peyman |
| 2006/0271186 A1 | 11/2006 | Nishi et al. |
| 2007/0123982 A1 | 5/2007 | Yablonski et al. |
| 2007/0233037 A1 | 10/2007 | Gifford, III et al. |
| 2008/0046076 A1 | 2/2008 | Rombach |
| 2008/0097459 A1 | 4/2008 | Kammerlander et al. |
| 2008/0106698 A1 | 5/2008 | Dai et al. |
| 2008/0119864 A1 | 5/2008 | Deinzer et al. |
| 2008/0125862 A1 | 5/2008 | Blake |
| 2008/0129962 A1 | 6/2008 | Dai et al. |
| 2009/0234449 A1 | 9/2009 | De Juan, Jr. et al. |

FOREIGN PATENT DOCUMENTS

| | | |
|---|---|---|
| WO | 03/000154 | 1/2003 |
| WO | 03/017867 | 3/2003 |
| WO | 03/049646 | 6/2003 |
| WO | 2004/037122 | 5/2004 |
| WO | 2004/037127 | 5/2004 |
| WO | 2004/053568 | 6/2004 |
| WO | 2004/107024 | 12/2004 |
| WO | WO 2005/046516 | 5/2005 |
| WO | 2005/082285 | 9/2005 |
| WO | 2005/084587 | 9/2005 |
| WO | 2007/015640 | 2/2007 |
| WO | 2007/113832 | 10/2007 |
| WO | 2008/031231 | 3/2008 |
| WO | 2009/088448 | 7/2009 |

OTHER PUBLICATIONS

Burd et al. "Mechanics of accommodation of the human eye" Vision Research 39:1591-1595 (1999).
Chien et al. "Analysis of human crystalline lens accommodation" J. Biochem. 39:672-680 (2006).
Dubbelman, Vision Research 41:1867-1877 (2001).
http://www.biovision.cz/wiol-cf.pdf; Biovision web presentation.
Pasta et al. "Pseudoaccommodation of WIOL CF Hydrogel lenses" ASCRS 2006 San Francisco, CA Biovision PowerPoint presentation.
Wilson, Trans. Am. Ophth. Soc. 95:261-266 (1997).

* cited by examiner

| | Initial Radius (mm) | Final Radius (mm) | Curvature change (1/mm) | Power change (D) | Total zonular force (gram-force) | Diopter change per unit force (D/gram-force) |
|---|---|---|---|---|---|---|
| mod1 | 4.537 | 4.595 | -0.003 | -0.555 | 21.822 | 0.025 |
| mod2 | 4.537 | 4.883 | -0.016 | -3.118 | 20.252 | 0.154 |
| mod3 | 4.537 | 5.004 | -0.021 | -4.109 | 19.395 | 0.212 |
| mod4 | 4.537 | 4.595 | -0.003 | -0.555 | 2.101 | 0.264 |
| mod5 | 4.537 | 5.004 | -0.021 | -4.109 | 5.812 | 0.707 |
| | | | | | | |
| solid | 4.514 | 4.665 | -0.007 | -1.434 | 39.626 | 0.036 |

INTRAOCULAR, ACCOMMODATING LENS AND METHODS OF USE

REFERENCE TO PRIORITY DOCUMENT

This application claims priority of U.S. Provisional Patent Application Ser. No. 61/018,837 filed on Jan. 3, 2008. The disclosure of the Provisional Patent Application is hereby incorporated by reference in its entirety.

BACKGROUND

The present disclosure relates generally to the field of ophthalmics, more particularly to ophthalmic devices, including intraocular lenses (IOLs) such as accommodating intraocular lenses.

A healthy young human eye can focus an object in far or near distance, as required. The capability of the eye to change back and forth from near vision to far vision is called accommodation (see for example, Burd et al. "Mechanics of accommodation of the human eye" *Vision Research* 39:1591-1595 (1999); Chien et al. "Analysis of human crystalline lens accommodation" *J. Biomech.* 39:672-680 (2006)). Accommodation occurs when the ciliary muscle contracts to thereby release the resting zonular tension on the equatorial region of the capsular bag of the eye. The release of zonular tension allows the inherent elasticity of the lens capsule to alter to a more globular or spherical shape, with increased surface curvatures of both the anterior and posterior lenticular surfaces.

When the ciliary muscle is relaxed, the ciliary muscle moves into the disaccommodated configuration, which is posterior and radially outward from the accommodated configuration. The radial outward movement of the ciliary muscles creates zonular tension on the lens capsule to stretch the equatorial region of lens toward the sclera. The disaccommodation mechanism flattens the lens and reduces the lens curvature (both anterior and posterior). Such natural accommodative capability thus involves altering the shape of the lens to the appropriate refractive parameters for focusing the light rays entering the eye on the retina to provide both near vision and distant vision.

Intraocular lens implantation for cataracts is the most commonly performed surgical procedure in elderly patients in the U.S., Nearly three million cataract surgeries are performed each year in the U.S., with an additional 2.5 million surgeries in Europe and Asia. In conventional extracapsular cataract surgery, the crystalline lens matrix is removed leaving intact the thin walls of the anterior and posterior capsules—together with zonular ligament connections to the ciliary body and ciliary muscles. The crystalline lens core is removed by phacoemulsification through a curvilinear capsularhexis and replaced with an intraocular lens. Unfortunately, conventional IOL's, even those that profess to be accommodative, may be unable to provide sufficient axial lens spatial displacement along the optical axis or lens shape change to provide an adequate amount of accommodation for near vision.

Several attempts have been made to make intraocular lenses that provide the ability to accommodate. However, there is still a need for an accommodative intraocular lens that can adequately change shape to simulate the action of a natural lens.

SUMMARY

It would be advantageous to provide IOLs adapted for accommodating movement which can achieve an acceptable amount of accommodation.

In one aspect, there is disclosed an intraocular lens, comprising an optical element adapted to be implanted within the capsular bag of a human eye. The optical element includes one or more internal layers formed by one or more planes that are moveable relative to one another in order to effect the power of the optical element. In an embodiment, a femtosecond laser having a wavelength in the range of about 1100 nm to about 1200 nm is used to form the internal planes.

In another aspect, there is disclosed a method of forming an intraocular lens, comprising providing an optical body that is adapted to be implanted within the capsular bag of a human eye; and releasing energy at a location internal to the optical body to create one or more internal layers separated by planes, wherein the inner layers are moveable relative to one another in order to effect the power of the optical element.

In another aspect, there is disclosed an intraocular lens, comprising an optical element adapted to be implanted within the capsular bag of a human eye. The optical element includes one or more chambers that are filled with a material that changes shape in response to forces acting upon the material.

These general and specific aspects may be implemented using the devices, methods, and systems or any combination of the devices, methods and systems disclosed herein.

DETAILED DESCRIPTION

Figure 1:
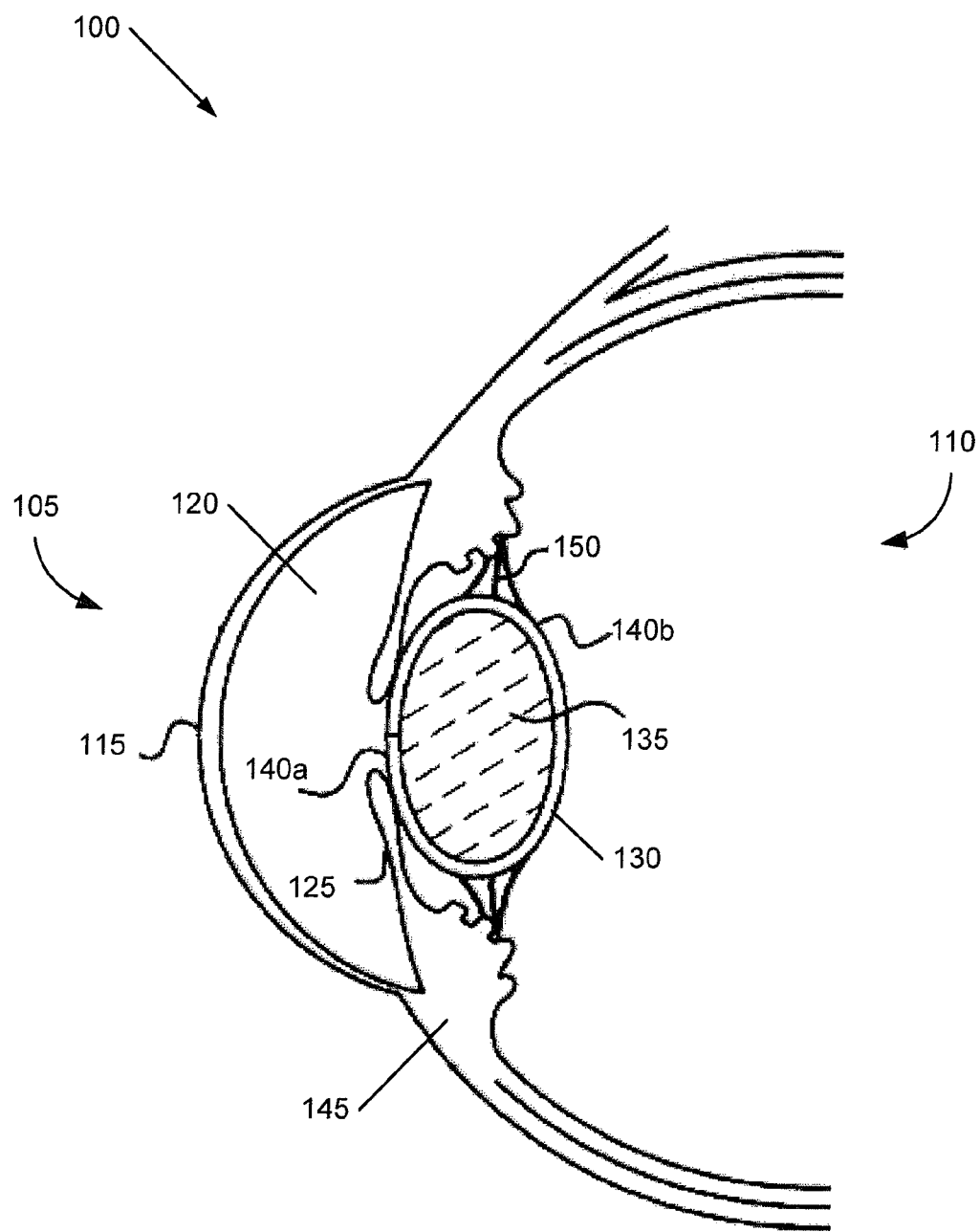
FIG. 1 is a cross-sectional view of a human eye.

Before the present subject matter is further described, it is to be understood that this subject matter described herein is not limited to particular embodiments described, as such may of course vary. It is also to be understood that the terminology used here in is for the purpose of describing particular embodiments only, and is not intended to be limiting. Unless defined otherwise, all technical terms used herein have the same meaning as commonly understood by one skilled in the art to which this subject matter belongs.

As will be apparent to those of skill in the art upon reading this disclosure, each of the individual embodiments described and illustrated herein has discrete components and features which may be readily separated from or combined with the features of any of the other several embodiments without departing from the scope of the subject matter described herein. Any recited method can be carried out in the order of events recited or in any other order which is logically possible.

Definitions

The terms zonular region or zonular contact region refer to the portion of the capsular bag that is typically contacted by or attached to the zonules. One way to describe the zonular contact region is as the portion of the capsular bag which is contacted by the zonules and which corresponds to that defined by the equatorial apices of the capsular bag and an orthogonal projection upon the capsular bag radius from the portion of the capsular bag contacted by the zonules. The determination of a capsular bag radius dimension in its accommodative or unaccommodative states can be made in various manners. For example, the determination of capsular bag radius dimension in its accommodative or unaccommodative states can be made using the Scheimpflug slit image technique (Dubbelman, Vision Research, 2001; 41:1867-1877), and IR video photography (Wilson, Trans. Am. Ophth. Soc. 1997; 95:261-266). The aforementioned references are incorporated herein by reference. Generally the zonular contact region is about 1.5-2.0 mm radially inward from the equatorial apices along the capsular bag radius.

The term percentage (X %) of zonular contact refers to the contact or attachment area along the capsular bag defined by the equatorial apices of the capsular bag and an orthogonal from a given percentage (%) of the capsular bag radius defining the zonular contact region. For example, contacting 50% of the zonular contact region refers to contacting that portion of the capsular bag that corresponds to the portion defined by the equatorial apices and a radii of 50% of the zonular contact region radii. For the purposes of example, if the zonular contact region has a radii of 1.5 mm, then the respective 50% would be that region defined by the equatorial apices and a contact region defined in part by the orthogonal at 0.75 mm or an orthogonal projection from 0.75 mm radially inward from the equatorial apices.

The term anterior portion of the zonular region refers to the most anterior portion of capsular bag contacted by the zonular region.

The term posterior portion of the zonular region refers to the most posterior portion of the capsular bag contacted by the zonular region.

The term shape changing optical element refers to an optical element that is made of material that enables the optical element to alter its shape, e.g. become one of more spherical in shape, thicker or focus on a closer object; or become more ovoid in shape, thinner or focus on a more distant object and thus alter the optical element's respective optics (alter the diopters of the resulting optical element).

The term accommodating shape refers to the shape of the optical element when at least one of the tensioning of the ciliary muscle of the mammalian eye, the zonules of the mammalian eye and a change in the vitreous pressure in the eye effect equatorial or polar distention of the capsular bag to effect a focusing upon a closer object. An accommodating shape is generally more spherical than the disaccommodating shape.

The term disaccommodating shape refers to the shape of the optical element when at least one of the relaxation of the ciliary muscle of the mammalian eye, the zonules of the mammalian eye and a change in the vitreous pressure in the eye and a comcomittant change to a more ovoid shaping of the capsular bag to effect a focusing upon a more distant object. A disaccommodating shape is generally more ovoid than the accommodating shape.

Capsulorhexis is the opening surgically made by puncturing, then grasping and tearing a hole in the anterior capsule. In a regular extracapsular cataract extraction (ECCE) procedure, a capsulorhexis is made in the anterior capsule and the cloudy cataract lens is extracted by phacoemulsification. The accommodative IOL described herein can be used for patients after cataract surgery. It can also be used for patients with only presbyopia, but without cataract.

The term diopter (D) refers to the reciprocal of the focal length of a lens in meters. For example, a 10 D lens brings parallel rays of light to a focus at (1/10) meter. After a patient's natural crystalline lens has been surgically removed, surgeons usually follow a formula, based on their own personal preference, to calculate a desirable diopter power (D) for the selection of an IOL for the patient to correct the patient's preoperational refractive error. For example, a myopia patient with −10 D undergoes cataract surgery and IOL implantation; the patient can see at a distance well enough even without glasses. This is because the surgeon has taken the patient's −10 D near-sightedness into account when choosing an IOL for the patient.

The term medially disposed within the capsular sac refers to being disposed within the generally equatorial region of the capsular bag, e.g., between the anterior and posterior portions of the capsular bag.

Exemplary Embodiments of Intraocular Lens

An accommodative intraocular lens (IOL) is adapted for surgical replacement of the natural crystalline lens in the human eye. FIG. 1 shows cross-sectional view of the human eye 100 prior to implantation of an IOL. The eye 100 includes an anterior portion 105 and a posterior portion 110. A cornea 115 is located on the anterior portion 105. The cornea 115 encloses and forms an anterior chamber 120, which contains aqueous fluid and is anteriorly bounded by an iris 125. A capsular bag 130 contains the natural crystalline lens 135. The capsular bag 130 includes an anterior wall 140a and a posterior wall 140b. The eye 10 further includes a ciliary muscle 145 attached to the capsular bag 130 via zonules 150. The vitreous humor is located posterior to the capsular bag 130 and anterior to the retina (not shown). The vitreous humor contains vitreous fluid.

The ciliary body 145 accomplishes ocular adjustments for focusing of objects viewed at different distances. In this regard, the ciliary body 145 acts on the capsular bag 130 and the natural crystalline lens 135 through the zonules 150. The ciliary body 145 contracts to allow the capsular bag 130 to return to a more spherical shape for viewing objects near to the viewer. When the ciliary body 145 retracts, the ciliary body 145 pulls on the zonules 150 to "flatten" the capsular bag 130 to permit objects at a distance to be viewed in proper focus. Thus, when the eye focuses, the capsular bag 140 changes shape to appropriately distribute the light admitted through the cornea 115 and the iris 125.

Figure 2:
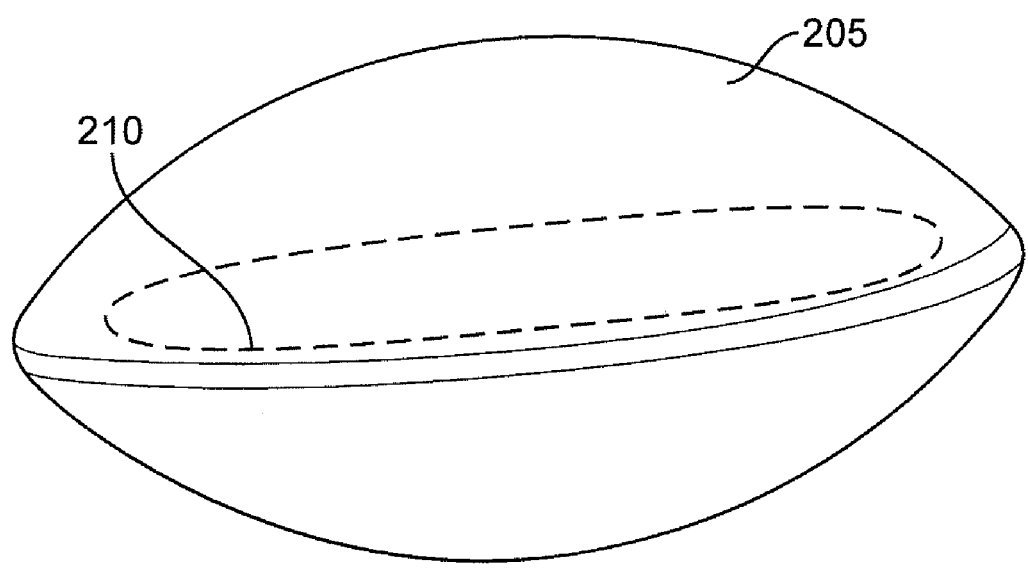
FIG. 2 shows an IOL that is adapted to be implanted within the capsular bag of a human eye.

FIG. 2 shows an IOL 205 formed of an optical body that is adapted to be implanted within the capsular bag 130 of a human eye 10. When positioned in the capsular bag 130, the IOL 205 changes shape in response to movement of the ciliary body 145 for focusing of objects viewed at different distances. In this regard, the IOL 205 includes one or more layers that are formed by internal surfaces or planes 210 (represented by a dashed line in FIG. 2) that are moveable relative to one another in order to affect the power of the IOL. When the planes move relative to one another, the focusing characteristics of the IOL 205 are changed to permit the lens to focus on objects at different distances. The IOL 205 in FIG. 2 has only a single internal plane 210 (or a pair of internal surfaces that are juxtaposed). However, it should be appreciated that the IOL 205 can include various quantities of internal planes of various shapes, sizes, and positions, as described in more detail below.

Each of the layers formed by the internal planes 210 comprises at least one surface formed internally within the IOL. The surfaces are juxtaposed with one another such that the surfaces can slide relative to one another. The presence of the layers formed by the internal planes makes the IOL 205 more susceptible to changes in shape than if the internal layers were not present. In an embodiment, at least some of the surfaces are in direct contact with one another and slidable relative to one another. In another embodiment, at least some of the surfaces are separated by a solid or liquid medium, such as hydrogel or silicone oil. Each of the surfaces can act as an individual lens body that refracts light. The lens material and the intervening medium each can have a refractive index that can be identical or generally identical such that reflection of light at the interface of the materials is minimized or eliminated. For example, an IOL can have lens material of silicone rubber having surfaces separated by a liquid medium of silicone oil. Silicone rubber and silicone oil have essentially the same refractive index thereby resulting in minimal light reflective effects of the juxtaposed surfaces. Similarly, any light reflective effects due to aberrations in the lens material and the creation of edges due to laser cuts within the lens would be minimized. The materials and methods used in the manufacture of the disclosed IOLs are discussed in more detail below.

The internal layers formed by the planes can have a property such that the IOL is inclined to change shape such as in a predetermined manner. The property that enables the shape change can vary and can include, for example, the structure, position, shape, size, pattern, Young's modulus, thickness, etc. The property can be relative to another layer or it can be absolute property. For example, the internal layers can be positioned, shaped, sized and/or patterned to maximize the amount of shape change in one or more locations of the IOL, such as within the center of the IOL. In an embodiment, at least one internal layer is positioned within a volume defined by 3 mm radius from the geometric center of the IOL.

Figure 3:
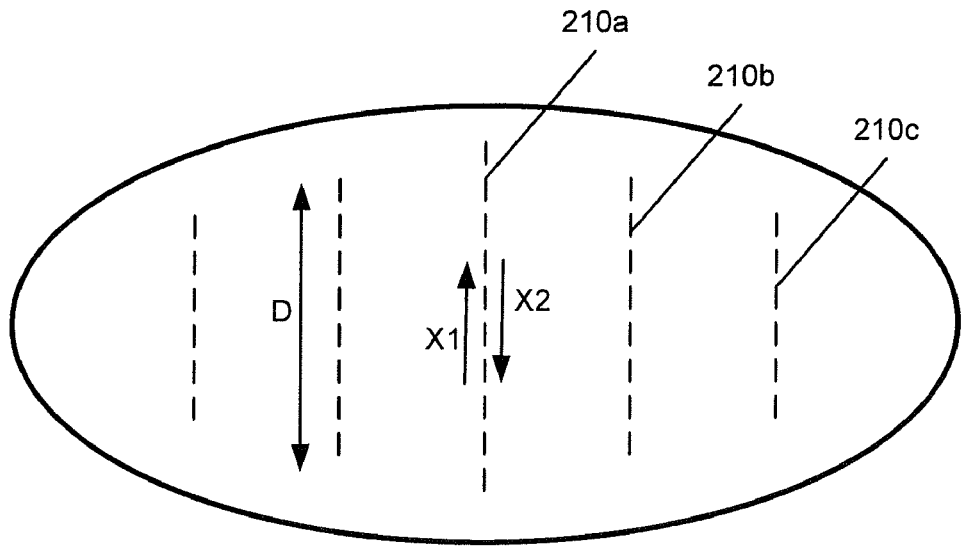
FIG. 3 shows a lateral, cross-sectional view of an IOL having internal planes.
Figure 4:
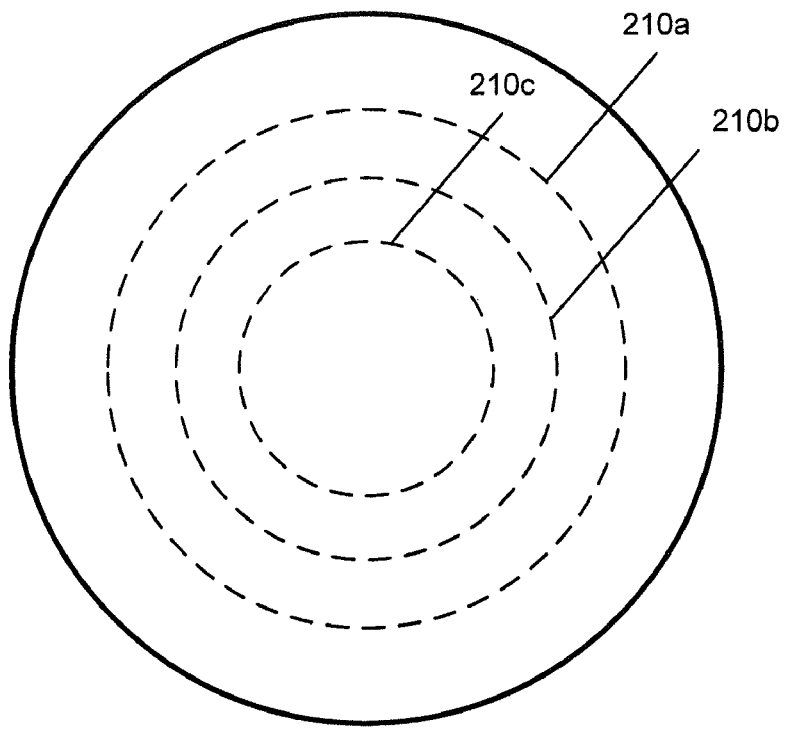
FIG. 4 shows a posterior, cross-sectional view of the IOL of FIG. 3.

FIG. 3 shows a lateral, cross-sectional view of an IOL 205 having internal layers formed by planes 210 that are arranged as a series of concentric, circular-shaped surfaces. When viewed from the side, the internal planes 210 are arranged in a side-by-side pattern with the planes 210 having a gradually reduced dimension D moving outwardly from the center of the IOL. As mentioned, the internal planes 210 define surfaces internal to the IOL wherein the surface on either side of each plane 210 can move relative to one another, as represented by the arrows X1 and X2 for plane 210a. The internal planes 210 can have any of a variety of contours including flat or curviplanar contours or combinations thereof. FIG. 4 shows a posterior, cross-sectional view of the IOL of FIG. 3. The internal planes 210 when viewed from the posterior viewpoint are concentrically-arranged circles.

As shown in FIG. 4, the outer perimeter edges of each layer formed by a plane 210 can be entirely contained within the internal volume of the IOL such that the outer surface of the IOL is uninterrupted by the presence of the internal plane. Alternately, at least a portion of the outer edge of an internal plane can extend to the outer surface of the IOL such that the plane forms a cleavage on the outer surface of the IOL.

With reference again to FIG. 3, the layers formed by internal planes 210 are shown as being generally parallel to one another. However, it should be appreciated that the internal planes 210 can be arranged in non-parallel relationships.

Figure 5:
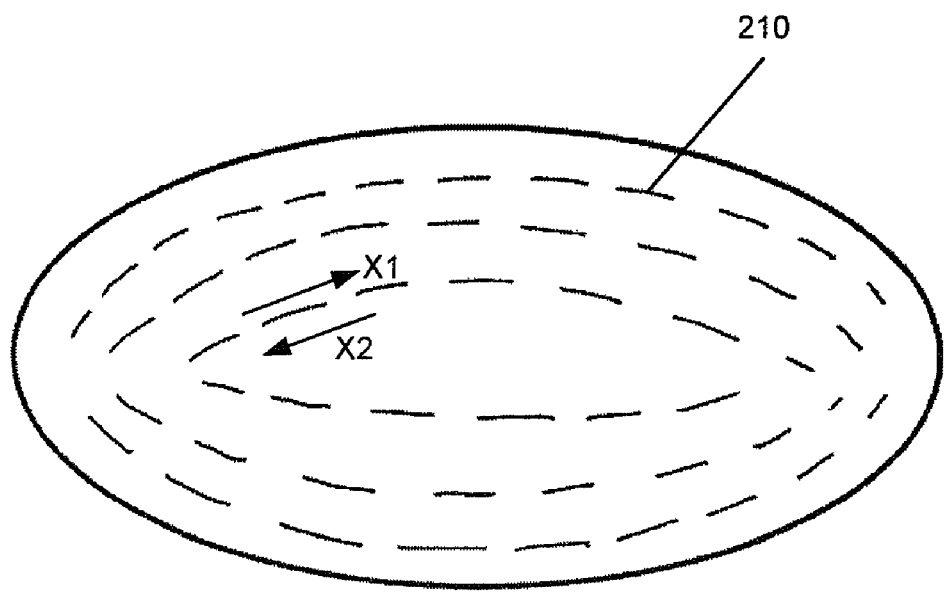
FIG. 5 shows a lateral, cross-sectional view of another embodiment of an IOL having internal planes.
Figure 6:
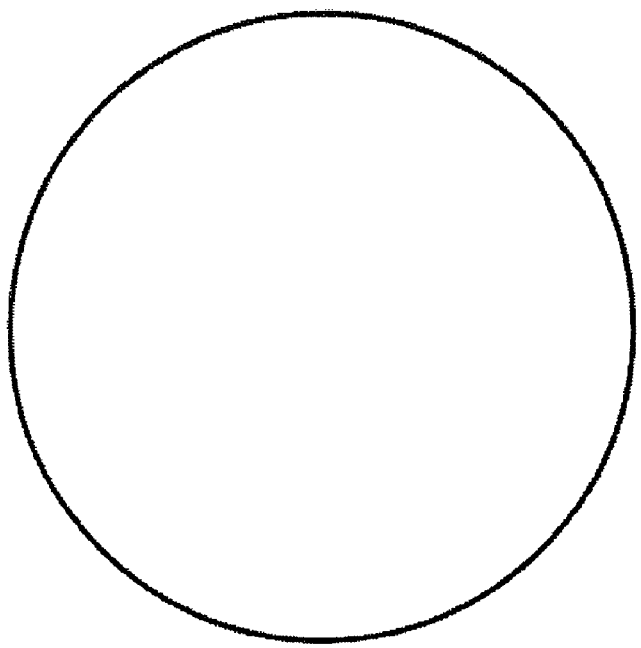
FIG. 6 shows a posterior, cross-sectional view of the IOL of FIG. 5.

FIG. 5 shows a lateral, cross-sectional view of an IOL 205 having layers formed by internal planes 210 that are arranged as a series of concentric spherical or partial spherical surfaces within the internal volume of the IOL. In other words, the internal planes 210 are arranged in an "onion skin" fashion of gradually reducing spheres. It should be appreciated that the internal planes in the embodiment of FIG. 5 are not necessarily spherical but can be any type of concentrically-arranged three-dimensional shapes. As mentioned, the planes 210 form juxtaposed surfaces that are adapted to move relative to one another as exhibited by the arrows X1 and X2 in FIG. 5. The movement can be three-dimensional in that the surfaces can slide relative to one another along a plane defined by the planes themselves. In an embodiment, the surfaces can also move toward and away from one another. FIG. 6 shows a posterior, cross-sectional view of the IOL of FIG. 5.

Figure 7:
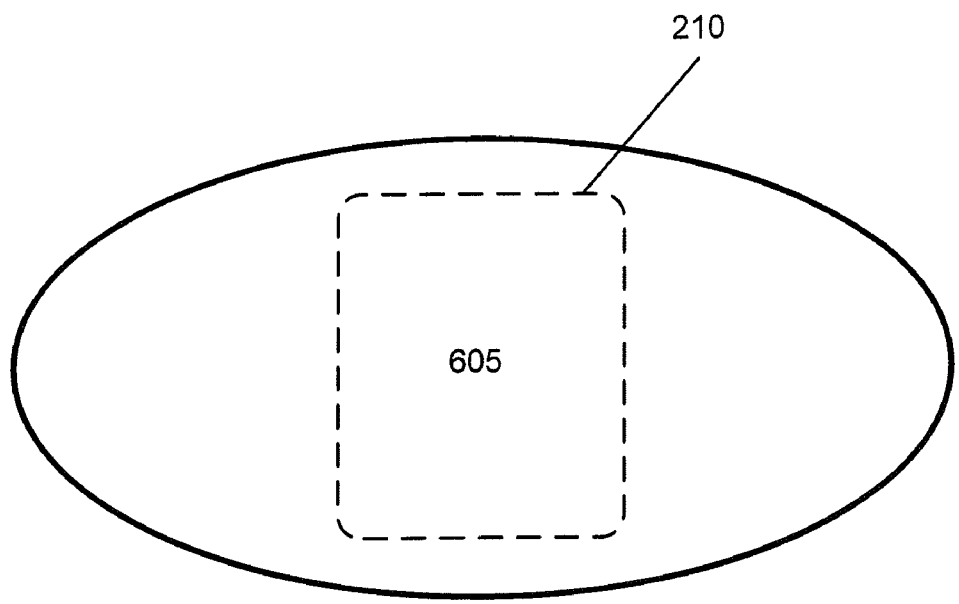
FIG. 7 shows a lateral, cross-sectional view of another embodiment of an IOL having internal planes.
Figure 8:
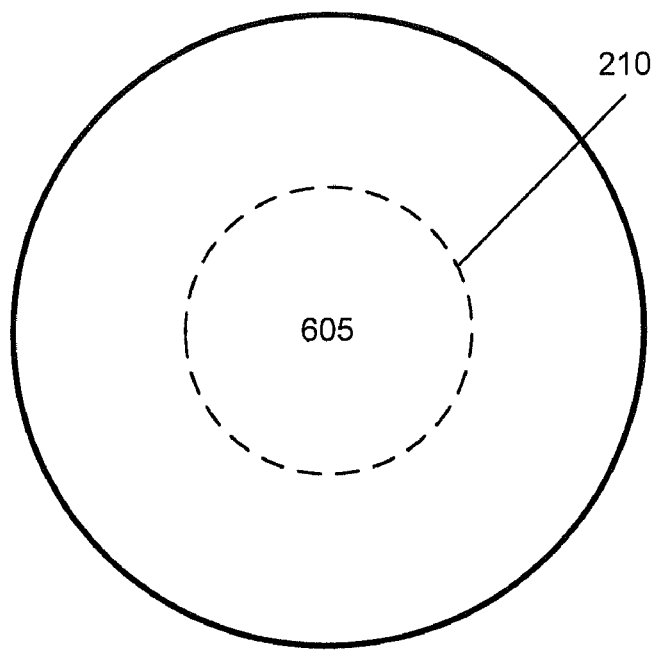
FIG. 8 shows a posterior, cross-sectional view of the IOL of FIG. 7.
Figure 9:
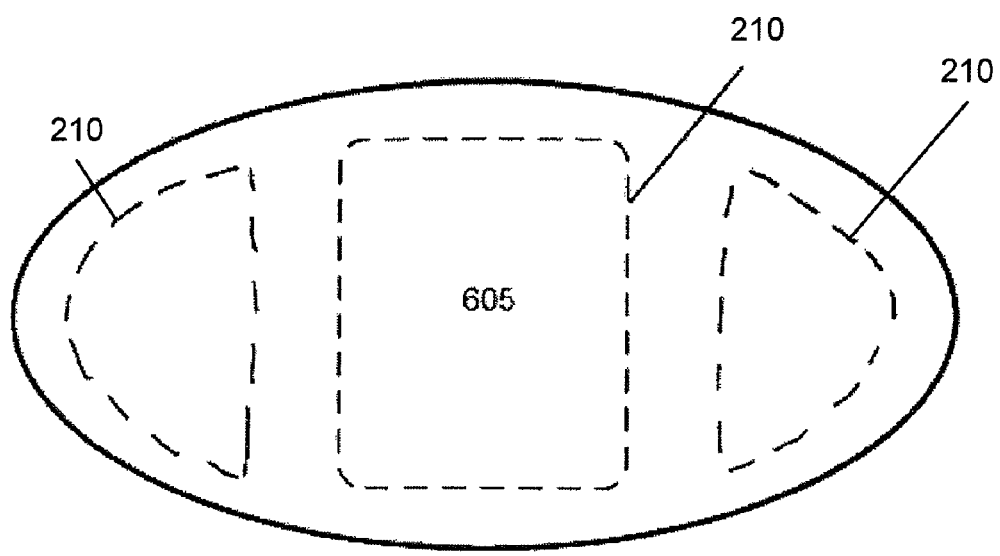
FIG. 9 shows a lateral, cross-sectional view of another embodiment of an IOL having internal planes.
Figure 10:
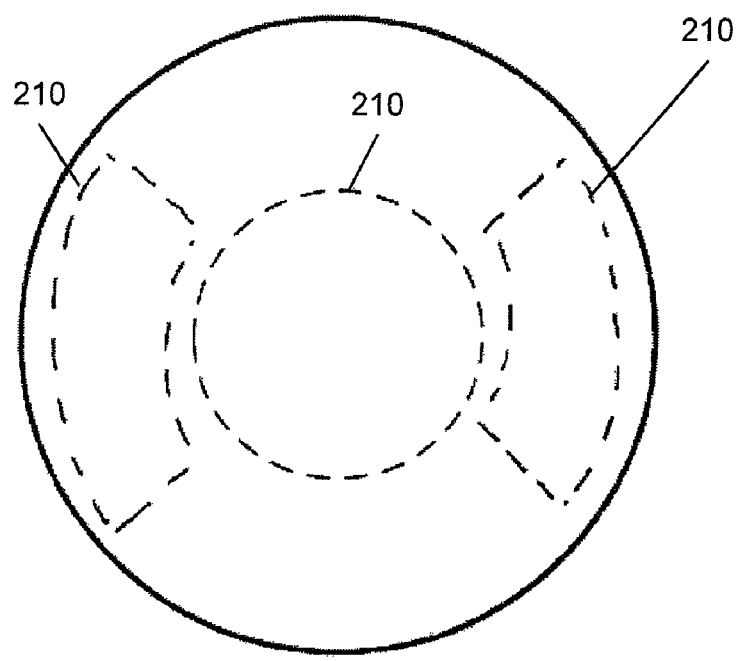
FIG. 10 shows a posterior, cross-sectional view of the IOL of FIG. 9.

FIG. 7 shows a lateral, cross-sectional view of another embodiment of an IOL 205 wherein a layer formed by an internal plane 210 forms at least one internal core member 605 within the IOL. The core member 605 can be defined by the internal plane 210 such that the surface of core member 605 can be movable relative to the remainder of the IOL 205. As shown in the posterior, cross-sectional view of FIG. 8, the core member 605 can be circular in cross-section from a posterior viewpoint, although the shape of the core member can vary. FIGS. 9 and 10 show lateral and posterior cross-sectional views, respectively, of an IOL having internal planes that form multiple core members 605. The internal planes 210 can be used to form any number of core members 605 of various shapes within the IOL 205.

The layers formed by internal plane(s) 210 can be formed within the interior of the IOL 205 in various manners. In an embodiment, lenses such as those manufactured by Biovision (WIOL™ C/CF; WIOL™ USI; Biovision s.r.o.; Prague, Czech Republic) can be modified using any number or orientation of cuts in the lens to form internal planes that achieve movement during accommodation (Pasta et al., "Pseudoaccommodation of WIOL CF Hydrogel lenses" ASCRS 2006 San Francisco, Calif. PowerPoint presentation; http://www-.biovision.cz/wiol-cf.pdf; Biovision Web Presentation). In an embodiment, an energy source can be used to form the interior planes. An applicator can be coupled to the energy source and energy focused within an interior region of the IOL 205. A level of energy released at a desired location or series of locations within the IOL can be sufficient to cleave a plane interior to the IOL and thereby form the internal planes 210. The release of energy can be guided along a contour or pathway such that energy is released to cleave a plane of a desired shape within the IOL.

Figure 11:
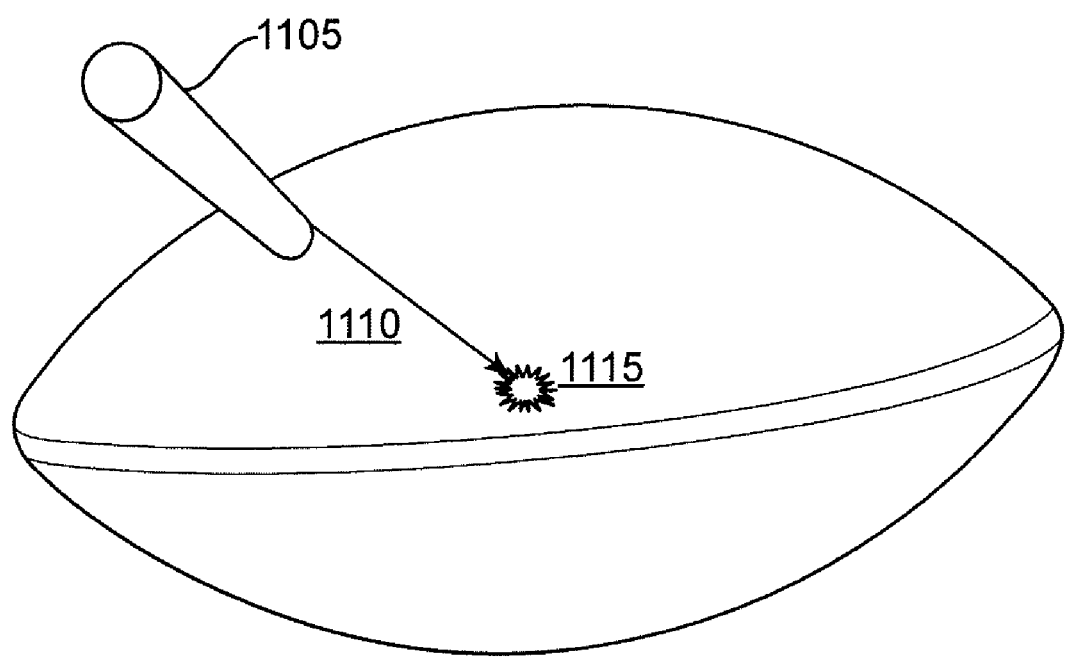
FIG. 11 shows a schematic representation of internal planes being formed in an IOL.

This process is represented schematically in FIG. 11, wherein an applicator 1105 releases a stream of energy 1110 into the IOL. The stream of energy can be focused at an internal location 1115 such that a sufficient level of energy is released at the location 1115. The IOL can be thereby cleaved at the location 1115 to form at least a portion of the internal plane.

In an embodiment, the energy source can be a laser used to form the internal plane 210 that forms the layer. Any type of laser that can be focused very precisely to achieve cleavage over a small volume of the IOL can be used. The laser can be configured to form an internal cleavage in the IOL without affecting the outer surface of the IOL. In an embodiment, a femtosecond laser having a wavelength in the range of about 1100 nm to about 1200 nm is used to form the internal plane. In an embodiment, the lens can undergo a power change of approximately 0.5 diopters to approximately 5 diopters.

Additional Embodiments

In another embodiment, the lens is adapted to change from a first shape to a second shape during implantation into the lens capsule or after the lens has been implanted in the lens capsule. The shape change can occur automatically, such as in response to a change in temperature, or it can occur upon manual activation by a clinician. For example, the lens may be manufactured of a material that is adapted to undergo a shape change in response to a predetermined stimulus.

In one embodiment, the lens can be manufactured in the accommodated state and implanted into the lens capsule. During or after implantation into the lens capsule, the lens undergoes a shape change to conform to the shape of the capsule. Some exemplary materials are hydrogel, acrylic and silicone. In the case of the lens being manufactured of hydrogel, the lens can be hydrated after implantation into the lens capsule to cause the lens to change shape, such as to conform to the shape of the capsule. The lens may be bonded to the capsule so that the lens moves with the capsule during ciliary muscle contraction and relaxation.

Figure 12:
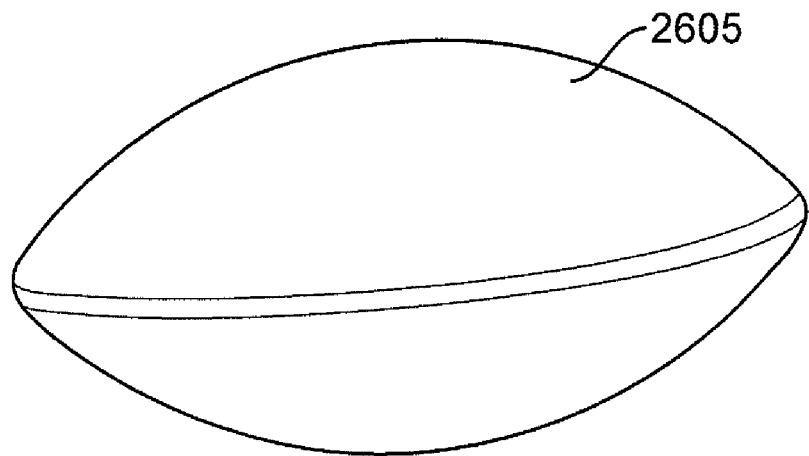
FIG. 12 shows a perspective view of another IOL that is adapted to be implanted within the capsular bag of a human eye.
Figure 13:
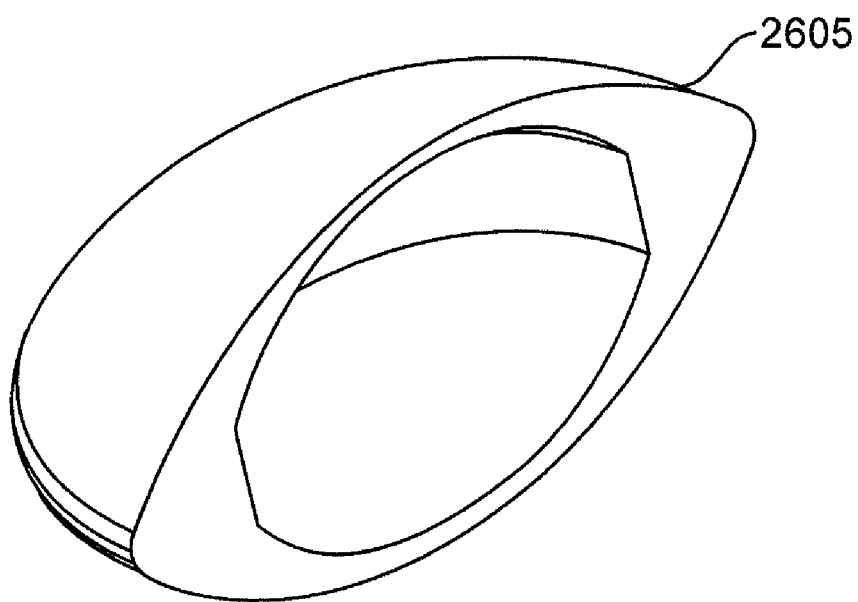
FIG. 13 shows a cross-sectional view of the IOL of FIG. 12.

FIG. 12 shows a perspective view of an IOL 2605 in an accommodated state. FIG. 13 shows a cross-sectional view of the IOL 2605. The IOL 2605 has an internal chamber that provides the IOL 2605 with a flexible nature that permits or encourages a shape change. The chamber can optionally be filled with a material that changes shape in response to forces acting upon the material. The material can be a liquid, a gas, or a solid, including a gel. Possible materials include, but are not limited to, air, silicone, oil, and hydrogel. The calculation of the lens power takes into account the type of material that is used to fill the chamber, to account for the optical interaction between the material and the inner surface of the chamber as well as the outer surface of the lens. In this regard, the refractive indices of the material in the chamber and the material of the lens can be selected to achieve a desired lens power. For example, the lens material and the material in the chamber can be selected to have refractive indices that are identical or generally identical such that reflection of light at the interface of the materials is minimized or eliminated.

Figure 14:
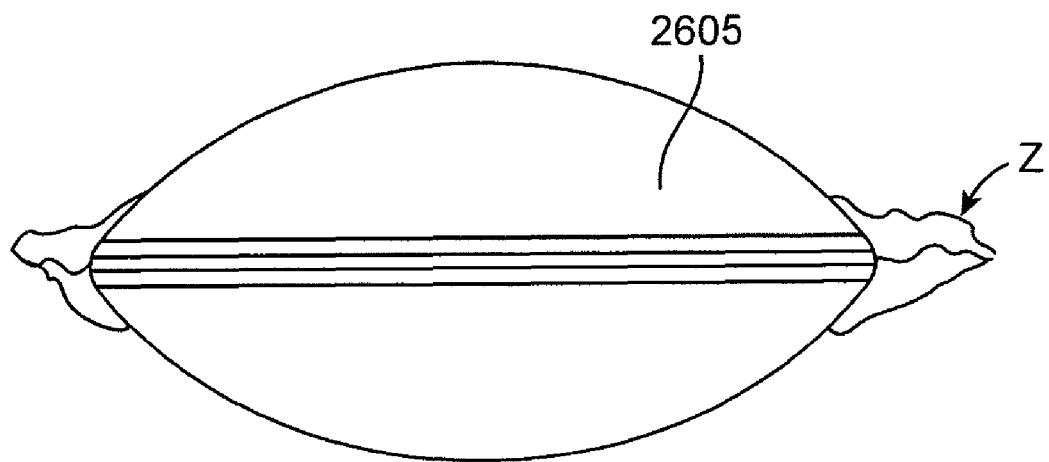
FIG. 14 shows a lateral view of the IOL in FIG. 12 in the accommodated state.
Figure 15A:
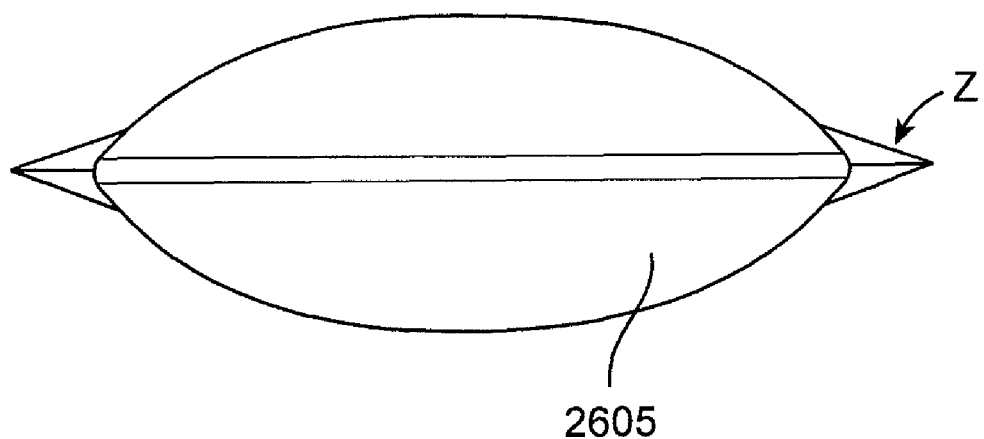
FIG. 15A shows a lateral view of the IOL in FIG. 12 in a disaccommodated state.

FIG. 14 shows a lateral view of the IOL 2605 in the accommodated state such that the zonules Z are relaxed. In FIG. 15A, the zonules Z are tensioned so that the IOL 2605 is in the unaccommodated state. Note that the IOL 2605 has taken on a flattened shape with respect to the accommodated state.

Figure 15B:
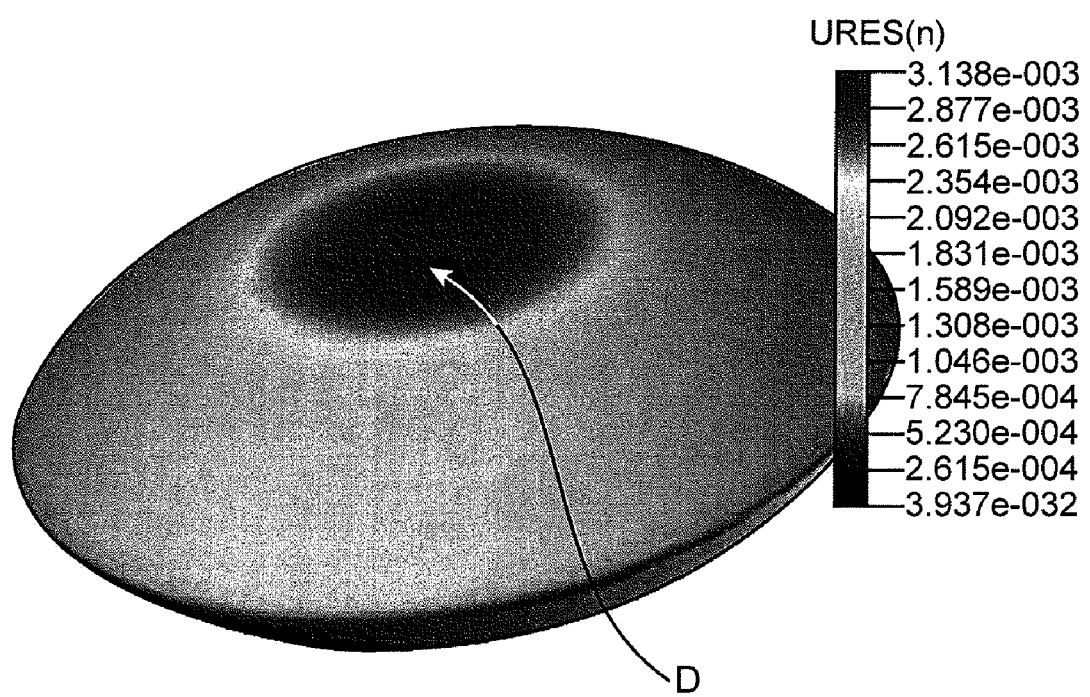
FIG. 15B shows a representative displacement of the IOL in FIG. 12 during disaccommodation.

FIG. 15B shows a representative displacement of the IOL 2605 as the zonules tense. As mentioned, the IOL flattens as the zonules tense. The IOL can be adapted to undergo different displacement or shape changes in different regions of the lens. For example, in the embodiment of FIG. 15B, the IOL undergoes a relatively large displacement D in the central anterior region.

Figure 16:
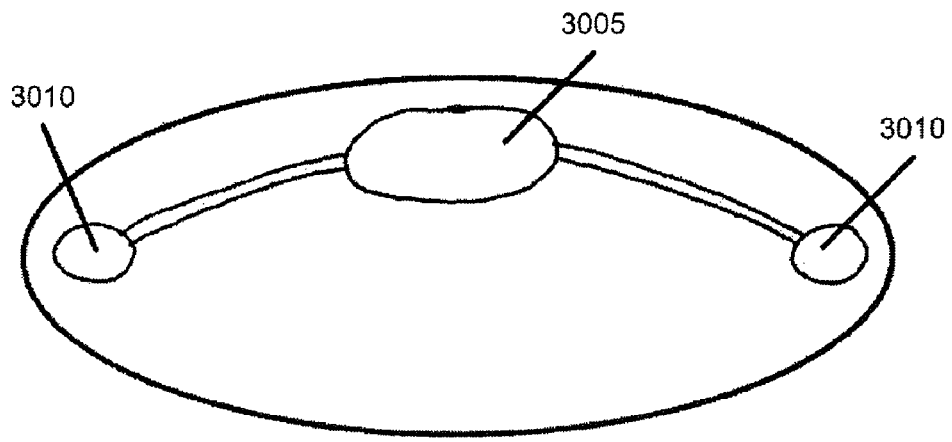
FIG. 16 shows a cross-sectional view of another embodiment of an IOL.

In yet another embodiment, the IOL includes one or more chambers that are filled with a flowable material, such as hydrogel or silicone oil. The material can flow from one chamber to one or more other chambers in response to stimuli. The flow of material between the chambers causes the IOL to undergo a shape change. For example, FIG. 16 shows a cross-sectional view of an IOL having a central chamber 3005 and one or more lateral chambers 3010 that are fluidly connected to the central chamber 3005. A flowable material resides in one or more of the chambers. In FIG. 16, the IOL is in an accommodated state such that all or a majority of the flowable material resides in the central chamber 3005. This causes the central chamber to have an expanded state relative to the lateral chambers 3010.

Figure 17:
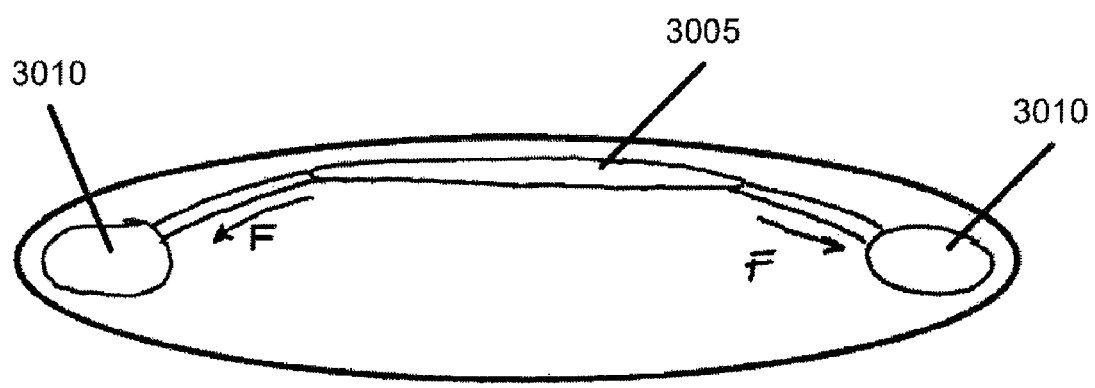
FIG. 17 shows a cross-sectional view of the IOL of FIG. 16 in the disaccommodated state.

In response to stimuli, the flowable material flows out of the central chamber 3005 as represented by arrows F in FIG. 17. The material flows into the lateral chambers 3010 to expand the lateral chambers 3010. This causes the IOL to flatten in shape.

Figure 18:
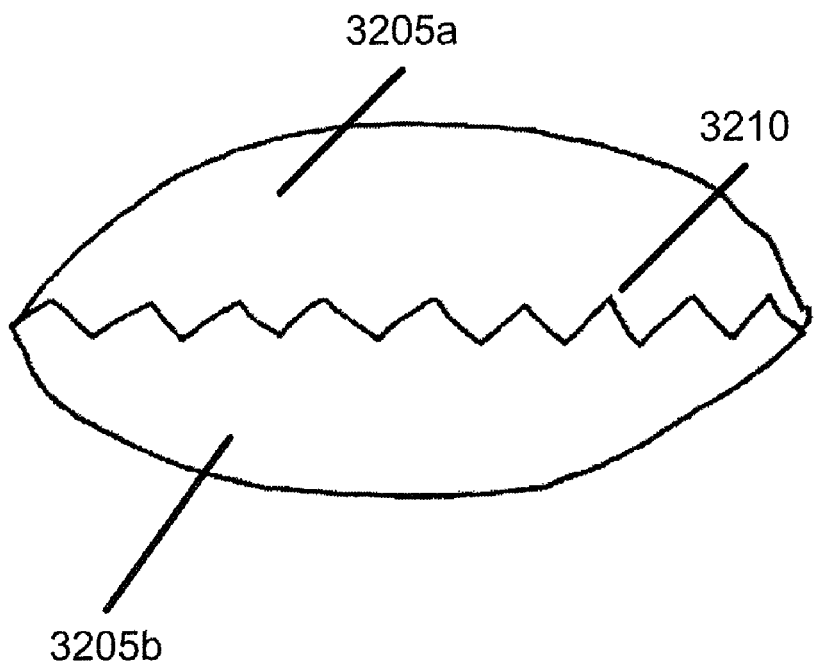
FIGS. 18 and 19 show another embodiment of an IOL.
Figure 19:
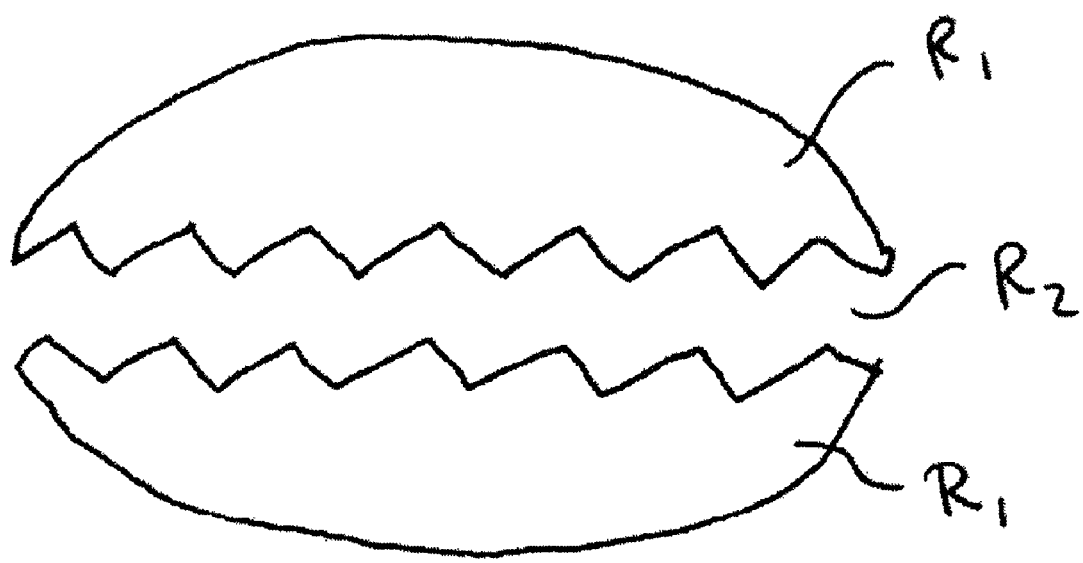

FIGS. 18 and 19 show another embodiment of an IOL comprised of two or more pieces 3205a and 3205b that collectively form a fresnel lens region 3210. The pieces each have a respective refractive index that can be the same or different from one another. When implanted in the eye, the two pieces are adapted to separate from one another, as shown in FIG. 19, or to move toward one another, as shown in FIG. 18, in response to zonular tension or lack thereof. When separated from one another as shown in FIG. 19, a space can form between the two pieces 3205a and 3205b wherein the material within the space has a refractive index different than the refractive index of the material from which the pieces are formed. The change in refractive index effectively forms a lens between the two pieces of the IOL.

The IOL can be manufactured using a variety of materials including, but not limited to silicone; silicone acrylate; acrylic; hydrogel (including urethanes, acrylamides, silicones, acrylics, polysaccharides, poly(N-vinylpyrrolidones), poly(hydroxyethylmethacrylate), acrylonitrile (AN) copolymers; polyacrylonitrile (PAN) polymers; PAN homopolymers; hydrophilic co-monomers (including acrylamide, vinyl pyrrolidone, styrene sulfonic acid, vinylsulfonic acid etc.); hydrophilic polymers; hydrophobic co-monomers (including alkyl acrylates or methacrylates, styrene, vinylchloride, methylstyrene, vinylpyridine etc.); hydrophobic polymers; and polymethylmethacrylate (PMMA). Exemplary materials used in the manufacture of IOLs are described in U.S. Pat. Nos. 6,232,406; 6,451,922; and 6,617,390, each of which are incorporated by reference herein.

The IOL can also be manufactured using a variety of methods and manufacturing processes. For example, the IOLs disclosed herein can be manufactured by shaping methods such as extrusion, casting, molding (including injection molding, compression molding, insert molding, etc.), dipping, spinning or similar shaping method. The IOLs disclosed herein can also be shaped using micromachining techniques, such as with a femtosecond laser. For example, a solid hydrogel lens can be sliced or cleaved with a laser thereby forming internal planes and a desired shape within the IOL. Other exemplary methods used in the manufacture and processing of IOLs are described in U.S. Pat. Nos. 5,674,283; 4,971,732; 4,893,918 and 4,806,287, each of which are incorporated by reference herein.

In an embodiment, the IOLs disclosed herein (205 or 2605) can be placed in situ by a procedure in which an incision is made in the eye. After the incision is formed, the original lens can be removed from the eye. The IOL 205 or 2605 can then be positioned within the eye and the incision closed. Any suitable procedure, including procedures in which the original lens or a portion of the original lens is not removed, may be used. The IOL 205 or 2605 can be used in conjunction with existing contacts, glasses, the natural lens, another IOL or any other suitable optical device, or the IOL 205 or 2605 can be used alone. Further, the IOL 205 or 2605 can be positioned in any suitable chamber (e.g., anterior or posterior) or within any suitable tissue or structure. The IOL 205 or 2605 also can be attached to the existing or natural lens in any suitable manner, or the IOL 205 or 2605 can be detached from or replace the existing or natural lens.

EXAMPLE

Mechanical Analysis of Multilayered Accommodating IOLs

Multilayer IOL designs such as IOL 205, having internal planes 210 arranged as a series of concentric spherical surfaces within the internal volume of the IOL, as shown in FIG. 3, were analyzed in isolation to characterize the optical power change-to-equatorial force relationship. This analysis used nonlinear axissymmetric finite element modeling of a three-layer prototype.

Figures 20, 21:
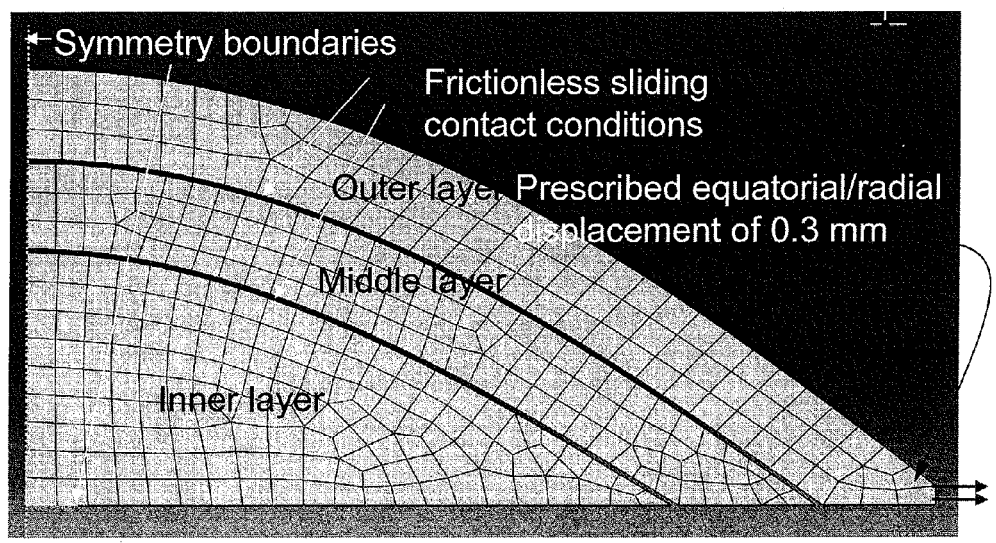
FIG. 20 shows a layered IOL model.
FIG. 21 shows the tabulated results for a solid, unlayered IOL and Models 1 through 5.

As shown in FIG. 20, the modeling assumed frictionless sliding/contact conditions and a prescribed equatorial/radical displacement of 0.3 mm.

Five models were developed, assuming different combinations of Young's modulus for elasticity. Young's modulus (E elasticity modulus), defined as the ratio of tensile stress to tensile strain, describes tensile elasticity, or the tendency of an object to deform along an axis when opposing forces are applied along that axis.

The following table shows the different combinations of Young's modulus used for each of the five examples of three-layered IOLs.

Table of Layered IOL Models' Elasticity Values (in MPa)

|  | Inner | Middle | Outer |
|---|---|---|---|
| Model 1 | 0.1 MPa | 0.1 MPa | 0.1 MPa |
| Model 2 | 0.01 MPa | 0.1 MPa | 0.1 MPa |
| Model 3 | 0.01 MPa | 0.01 MPa | 0.1 MPa |
| Model 4 | 0.01 MPa | 0.01 MPa | 0.01 MPa |
| Model 5 | 0.003 MPa | 0.003 MPa | 0.03 MPa |

The curvature per power ratio is based upon an aperture of 2.5 mm in diameter and a refractive index difference of 0.1. The optical power change is calculated using the following formula, where DP is the diopter power change, $n_2 - n_1 = 0.1$, and R is the radius in mm:

$$DP = 2*1000*(n_2 - n_1)*\left[\frac{1}{R_{final}(mm)} - \frac{1}{R_{init}(mm)}\right]$$

Figure 22:
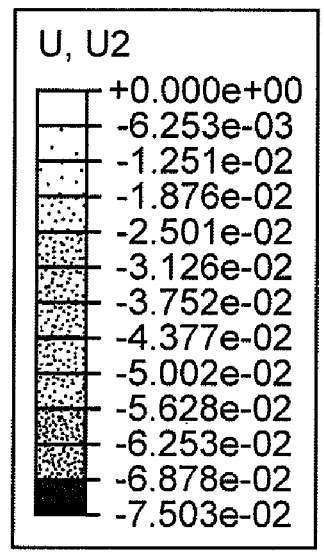
FIGS. 22-26 show various IOL modeling characteristics.
Figure 22:
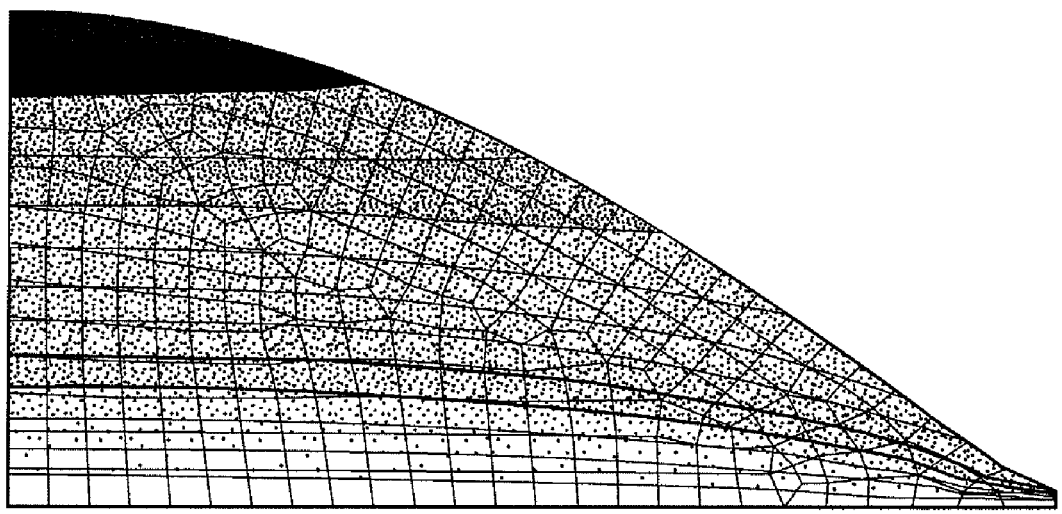
Figure 23:
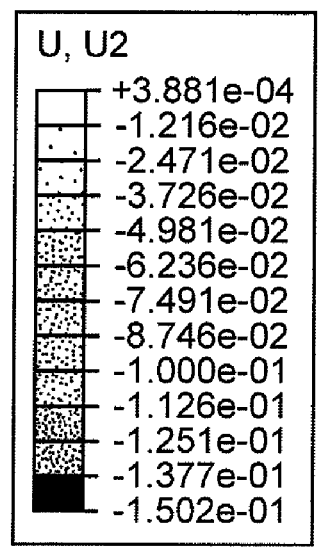
Figure 23:
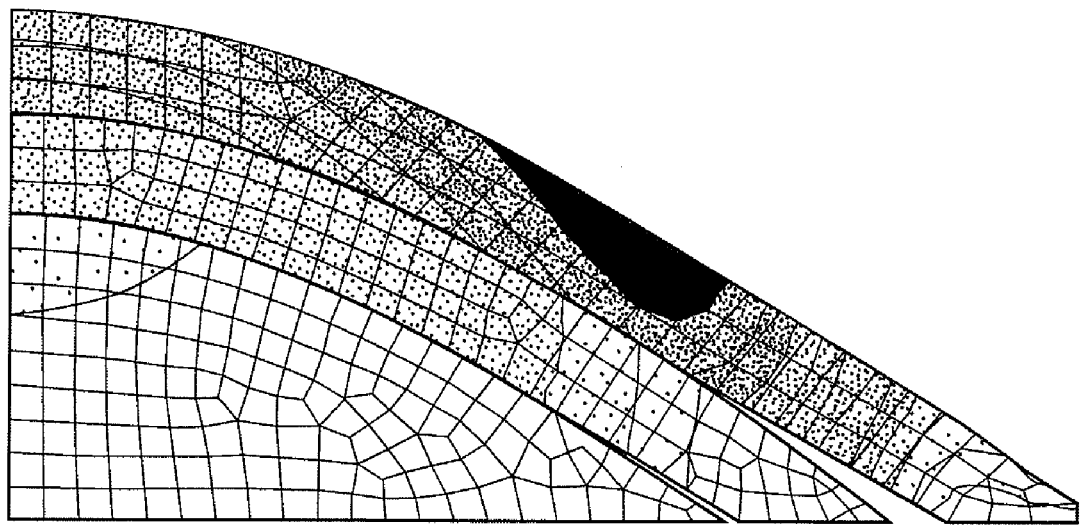
Figure 24:
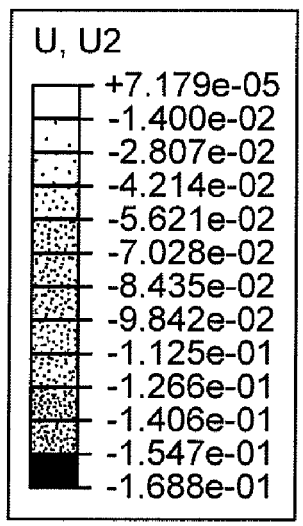
Figure 24:
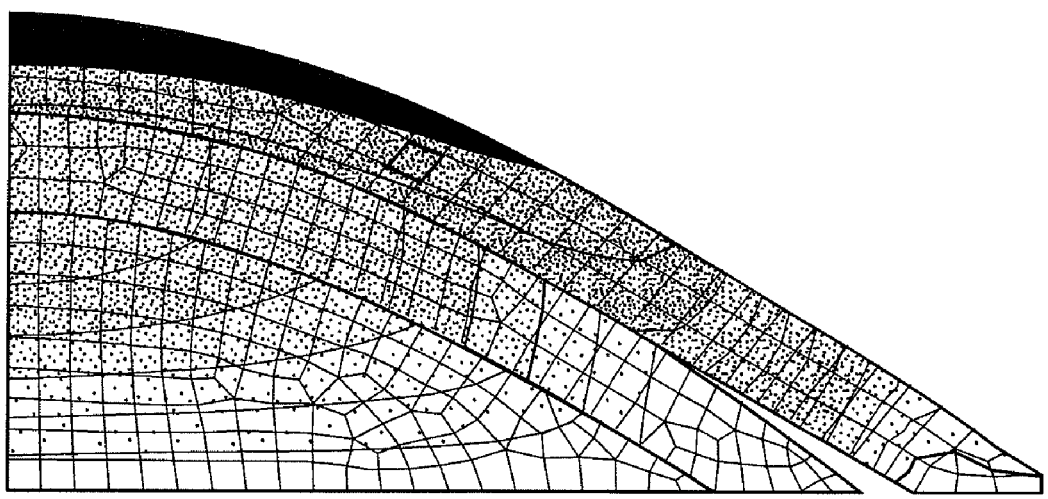
Figure 25:
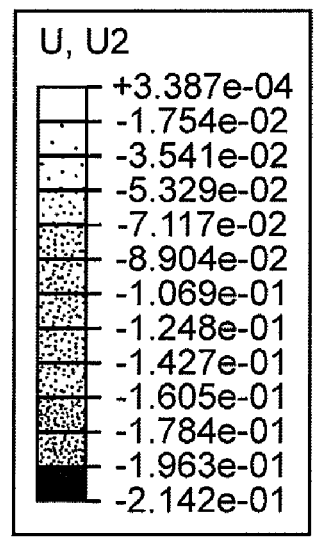
Figure 25:
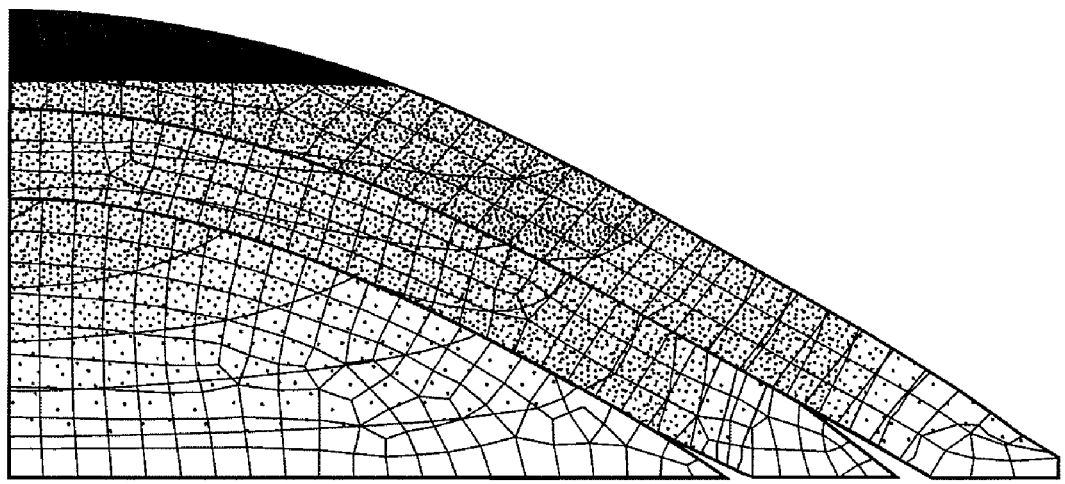
Figure 26:
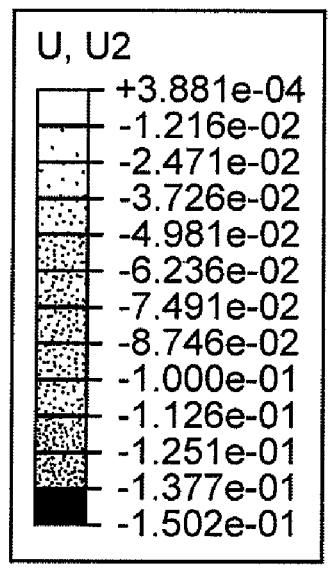
Figure 26:
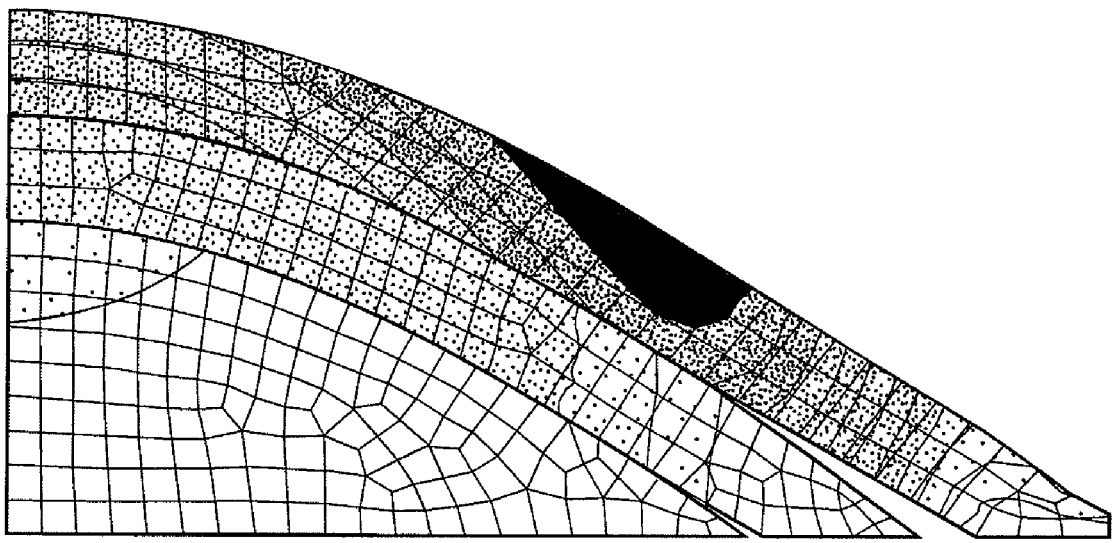

FIG. 21 shows the tabulated results for a solid, unlayered IOL and Models 1 through 5. FIG. 22 shows the vertical displacement contours (mm) for the solid section, FIG. 23 for Model 1, FIG. 24 for Model 2, FIG. 25 for Model 3 and 5, and FIG. 26 for Model 4.

A solid, unlayered IOL is the reference point for the analysis. It is observed that power is independent of Young's modulus; but dependent on the Poisson ratio (bulk modulus). Since the solid, unlayered lens is incompressible (Poisson ratio ~0.5), its performance is fixed. The solid, unlayered IOL gives a power change of −1.434 D and a diopter to force ratio of 0.036 D/gram-force.

With regard to the layered IOLs, it is observed that power is controlled by the ratio of the layers' Young's moduli; not their absolute values. For example, Models 3 and 5 give the same power change; in particular, the best results come from models with a relatively stiff outer layer.

The total force required to achieve a 0.3 mm radial displacement depends on the value of the outer layer's Young's modulus; thus, it is observed that Models 3 and 5 have different zonular force requirements.

The effect of changing the modulus ratios is nonlinear because of the sliding contact. Optimal design is achieved by controlling both layer moduli ratios and absolute values; for example, Model 5 produces −4 D power with less than 6 grams of zonular force.

The efficiency of the designs is given by the power per unit zonular force; for example, Model 5 is approximately 20 times more efficient than the solid section. In an unexpected result, Model 5 offers a power change that is 2.86 times larger than the unlayered, solid IOL under a 0.3 mm radial displacement, while the zonular force required to achieve that displacement in Model 5 is 0.15 times that of the solid, unlayered IOL.

Figure 27:
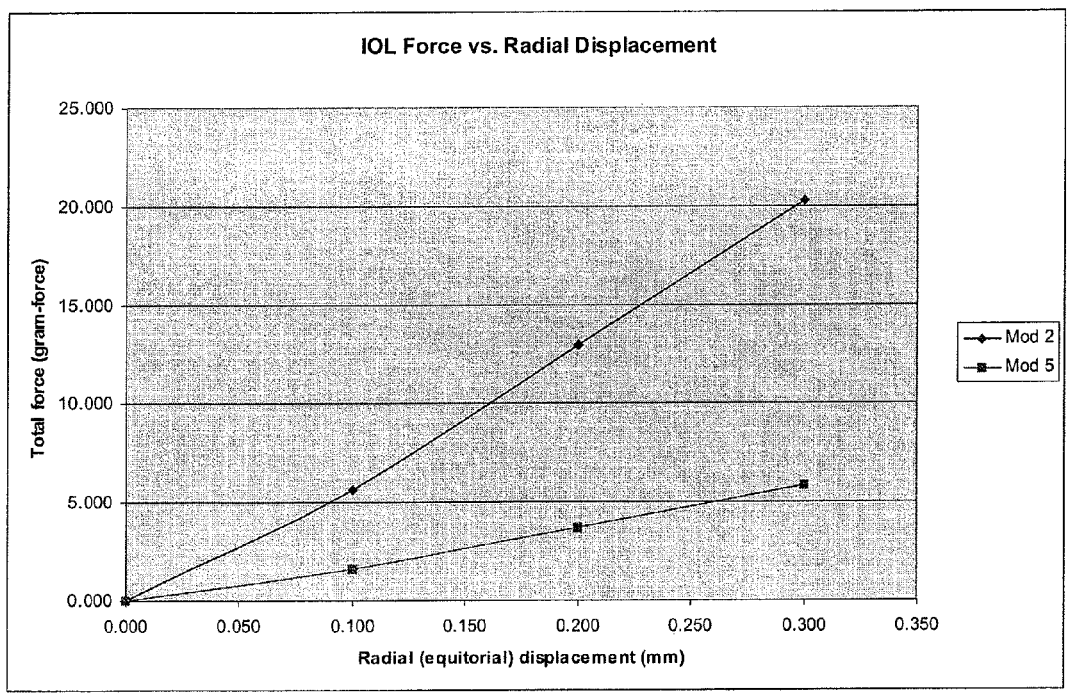
FIG. 27 shows a graph of the IOL force versus radial displacement for Models 2 and 5.
Figure 28:
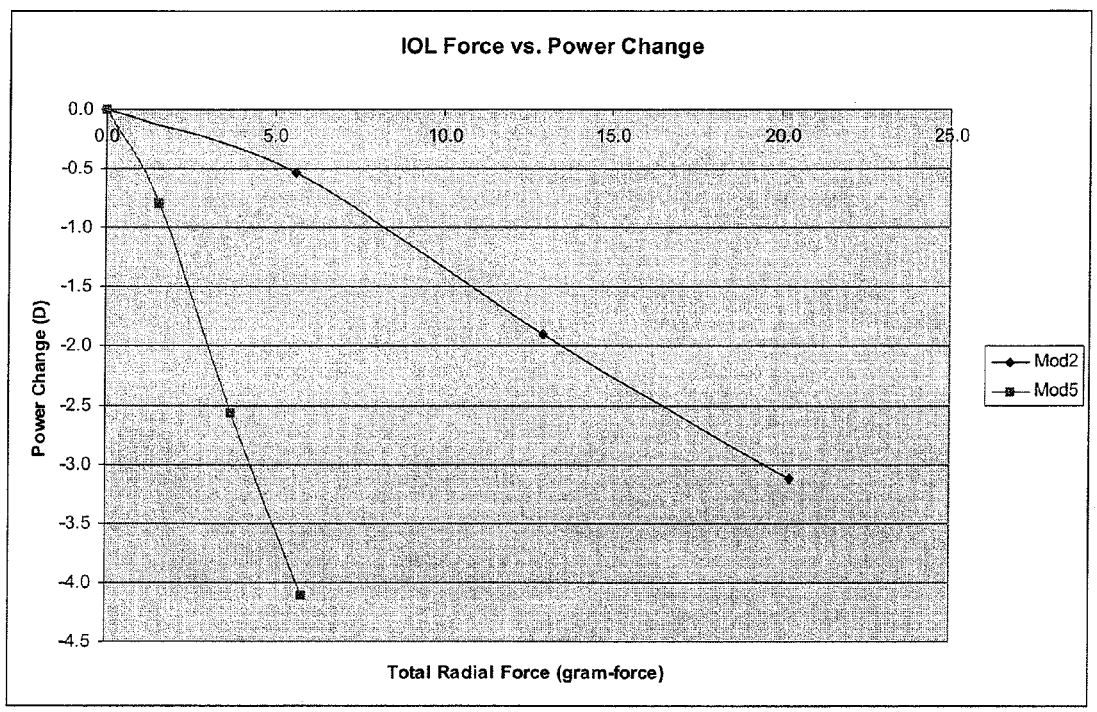
FIG. 28 shows a graph of the IOL force versus power change.
Figure 29:
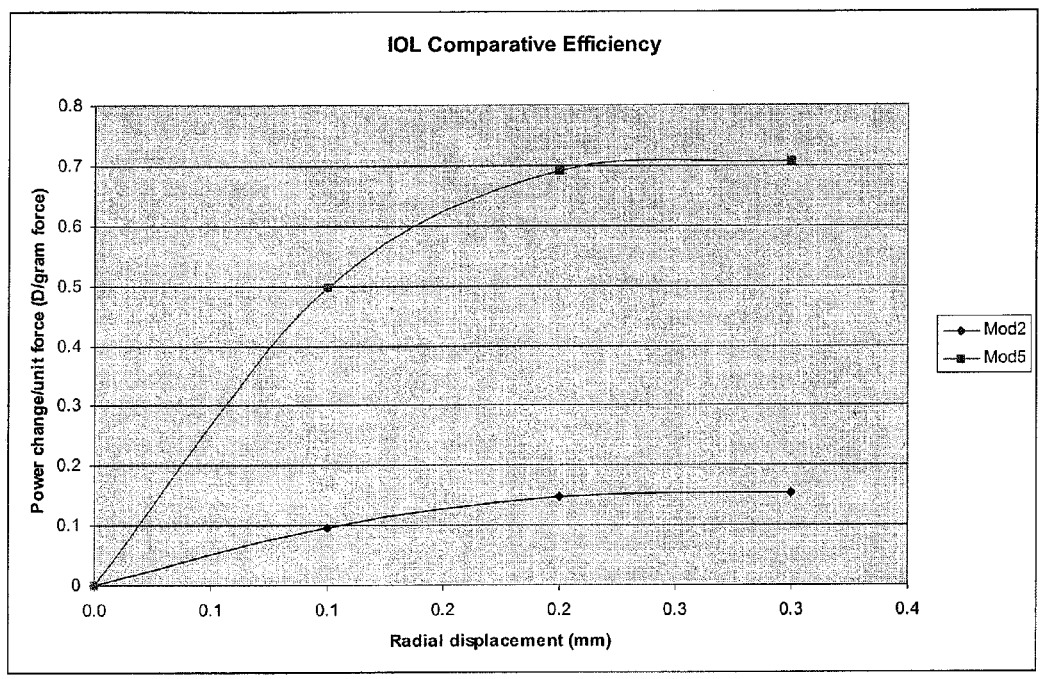
FIGS. 29-30 are graphs showing comparing the IOL efficiency of Models 2 and 5.
Figure 30:
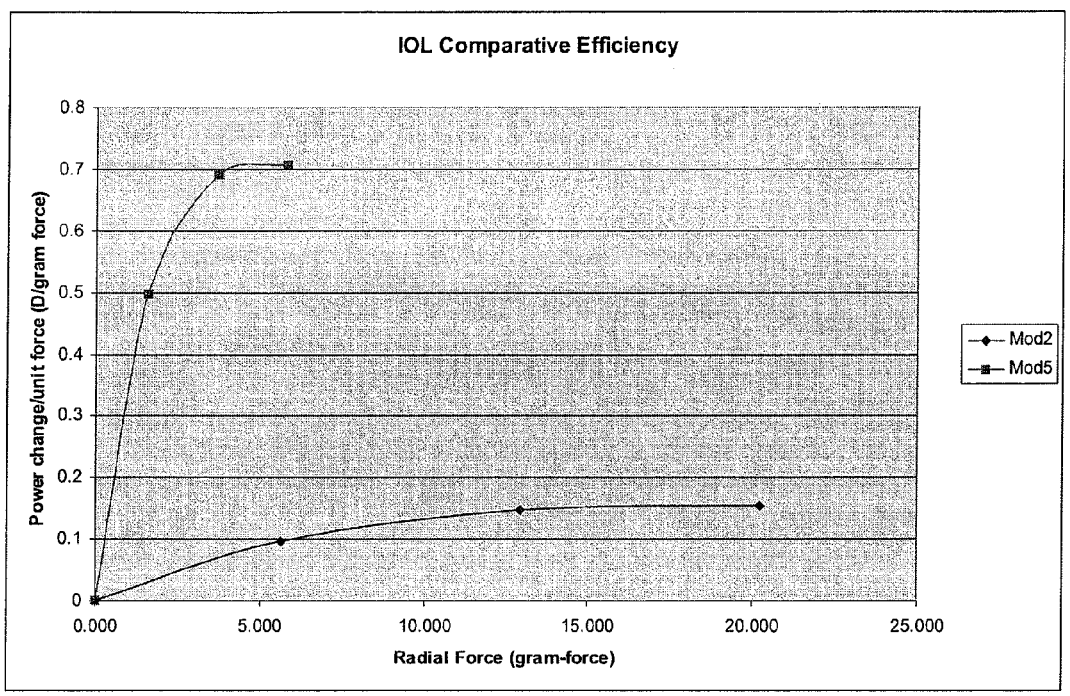

FIG. 27 shows a graph of the IOL force versus radial displacement for Models 2 and 5. Model 2 requires more force for the same amount of displacement than Model 5. FIG. 28 shows a graph of the IOL force versus power change. For the same amount of radial force, Model 5 produces a lot more power change. FIGS. 29-30 are graphs showing comparing the IOL efficiency of Models 2 and 5; Model 5 is considerably more efficient in producing diopter changes than Model 2.

Based upon the foregoing analysis, IOLs that are made from the same material are not very effective in producing diopter changes. The unexpected result is that, in order to increase the efficiency of the IOLs, the outer layer must be stiffer than the inner layers, as can be observed from the results obtained for Model 5.

IOLs of the type used in Model 5 can be obtained in various ways. For example, a femtosecond laser can be used to morcellate the inner layers, to decrease their bulk modulus, while the Young's modulus of the outer layer remains high.

Another alternative method of producing an IOL of the Model 5 type involves using a silicone outer layer, while injecting silicone oil into a hollow inner layer. Silicone oil has the same refractive index as silicone polymer, and thus the visual acuity through these IOLs will not become compromised.

Another method of producing IOLs of the Model 5 type comprises molding an inner layer of low Young's modulus material, and then overmolding the subsequent layers on top of the initial inner layer.

Although embodiments of various methods and devices are described herein in detail with reference to certain versions, it should be appreciated that other versions, embodiments, methods of use, and combinations thereof are also possible and within the scope of the claims. Therefore the spirit and scope of the appended claims should not be limited to the description of the embodiments contained herein. Certain features that are described in this specification in the context of separate embodiments can also be implemented in combination in a single embodiment. Conversely, various features that are described in the context of a single embodiment can also be implemented in multiple embodiments separately or in any suitable sub-combination. Moreover, although features may be described above as acting in certain combinations and even initially claimed as such, one or more features from a claimed combination can in some cases be excised from the combination, and the claimed combination may be directed to a sub-combination or a variation of a sub-combination. Similarly, while operations are depicted in the drawings in a particular order, this should not be understood as requiring that such operations be performed in the particular order shown or in sequential order, or that all illustrated operations be performed, to achieve desirable results.

Only a few examples and implementations are disclosed. Variations, modifications and enhancements to the described examples and implementations and other implementations may be made based on what is disclosed.

What is claimed is:

1. An intraocular lens, comprising:
an optical element adapted to be implanted in a human eye, wherein the optical element comprises a unitary structure having a plurality of surfaces extending through a portion of the structure and forming one or more concentric internal layers and an outer layer, wherein the concentric internal layers are surrounded by the outer layer at a first region and the concentric internal layers become the outer layer at a second region,
wherein each of the plurality of surfaces forms first and second juxtaposed internal surfaces that are slideably moveable relative to one another in order to effect the power of the optical element, and wherein the unitary structure is formed of only a single material.

2. A lens as in claim 1, wherein the first and second juxtaposed internal surfaces are in direct contact and slidable relative to each other.

3. A lens as in claim 1, wherein the first and second juxtaposed internal surfaces are separated by a solid, liquid, or gas medium.

4. A lens as in claim 3, wherein the medium is hydrogel or silicone oil.

5. A lens as in claim 4, wherein the medium and the optical element have identical refractive indices.

6. A lens as in claim 1, wherein a femtosecond laser is used to form the plurality of surfaces.

7. A lens as in claim 6, wherein the femtosecond laser has a wavelength in the range of about 1100 nm to about 1200 nm.

8. A lens as in claim 1, wherein at least one property of the concentric internal layers is adapted to maximize an amount of shape change in one or more locations of the lens.

9. A lens as in claim 8, wherein the at least one property is a thickness of a layer relative to another layer.

10. A lens as in claim 8, wherein the at least one property is a Young's modulus of a layer relative to another layer.

11. A lens as in claim 8, wherein the at least one property is a position of a layer relative to another layer.

12. A lens as in claim 1, wherein the optical element includes one or more chambers that are filled with a flowable material.

13. A lens as in claim 1, wherein the outer layer is stiffer than the one or more concentric internal layers at the first region.

14. A lens as in claim 1, wherein the optical element is adapted to be implanted within a capsular bag of a human eye.

* * * * *